United States Patent
Al-Majid et al.

(10) Patent No.: US 9,802,894 B2
(45) Date of Patent: Oct. 31, 2017

(54) α-GLUCOSIDASE INHIBITORS

(71) Applicant: KING SAUD UNIVERSITY, Riyadh (SA)

(72) Inventors: Abdullah Mohammed Al-Majid, Riyadh (SA); Mohammad Shahidul Islam, Riyadh (SA); Assem Barakat, Riyadh (SA); Muhammad Iqbal Choudhary, Riyadh (SA); Sammer Yousuf, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/868,994

(22) Filed: Sep. 29, 2015

(65) Prior Publication Data
US 2017/0088516 A1     Mar. 30, 2017

(51) Int. Cl.
*C07D 209/12*     (2006.01)

(52) U.S. Cl.
CPC ................... *C07D 209/12* (2013.01)

(58) Field of Classification Search
None
See application file for complete search history.

(56) References Cited

U.S. PATENT DOCUMENTS

| 7,625,933 B2 | 12/2009 | Liu et al. |
| 2013/0196991 A1 | 8/2013 | Ivachtchenko et al. |

OTHER PUBLICATIONS

Bartoli et al., Organocatalytic Asymmetric Friedel-Crafts Alkylation of Indole with α,β-Unsaturated Ketones. Organic Letters, 2007, 9, 1403-1405.*

Barakat et al., Highly enantioselective Friedel-Crafts alkylation of indoles with alpha,beta-unsaturated ketones with simple Cu(II)-oxazoline-imidazoline catalysts. Tetrahedron, 2013, 69, 5185-5192.*

Ito et. al., A medium-term rat liver bioassay for rapid in vivo detection of carcinogenic potential of chemicals. Cancer Science, 2003, 94, 3-8.*

Wang et al., Highly Enantioselective Synthesis of β-Heteroaryl-Substituted Dihydrochalcones Through Friedel-Crafts Alkylation of Indoles and Pyrrole. Chemistry—A European Journal. 2010, 16, 1664-1669.*

Rydzewski, Real World Drug Discovery 2008, 42-43.*

Barakat et al., "Highly Enantioselective Friedel-Crafts Alkylation of Indoles With α,β-Unsaturated Ketones With Simple Cu (II)-Oxazoline-Imidazoline Catalysts" Tetrahedron, 2013, 69, pp. 5185-5192.

* cited by examiner

*Primary Examiner* — Michael Barker
*Assistant Examiner* — Po-Chih Chen
(74) *Attorney, Agent, or Firm* — Richard C. Litman

(57) ABSTRACT

Novel α-Glucosidase inhibitors include propanone substituted indole ring-containing heterocyclic compounds, which are represented by Formula I:
Wherein

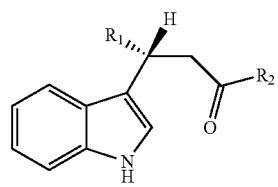

$R_1$ is thiophene, 2,4-di chloro phenyl, 2,6-di chloro phenyl, bromo phenyl, benzyl or nitrophenyl; and $R_2$ is an aryl group, or stereoisomers or pharmaceutically acceptable salts thereof.

9 Claims, 1 Drawing Sheet

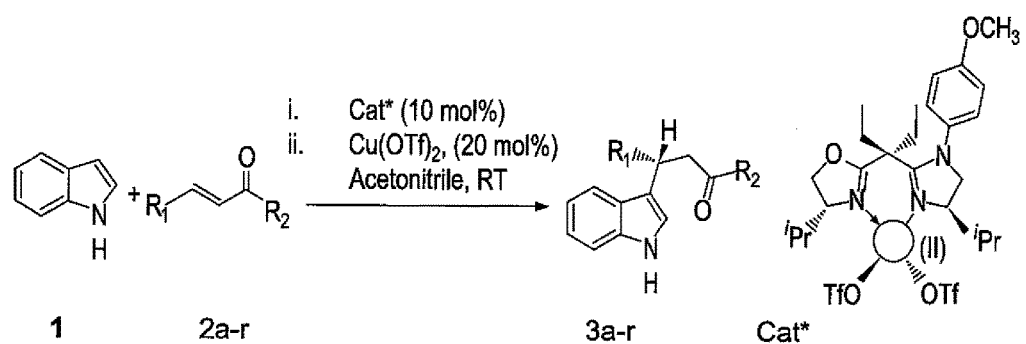

α-GLUCOSIDASE INHIBITORS

BACKGROUND OF THE INVENTION

1. Field of the Invention

The present invention relates to indole ring-containing heterocyclic compounds, and particularly to propanone-substituted indole ring-containing heterocyclic compounds, as novel α-glucosidase inhibitors.

2. Description of the Related Art

Indoles form a large class of heterocyclic compounds, found in many natural products, such as alkaloids, fungal metabolites and marine natural products. Indole myriad derivatives have therefore captured the attention of organic synthetic chemists. Indole and its analogs are known to possess a wide spectrum of biological activities. Several indole derivatives were reported as anticancer, antibacterial, anti-ulcerative, anti-platelet, anti-malarial, anti-leishmanial, antiviral, antioxidant, anti-rheumatoidal, anti-HIV, immunomodulator, anti-tubercular, inhibitors of chemical mediator's release and leukotriene $B_4$ tyrosinase and aldose (reductase activity).

Some of these compounds also possess anti-inflammatory and analgesic properties. They play a vital role in the immune system. Many indole derivatives are potent scavengers of free radicals. The immense biological activities of indole derivatives led to vigorous research to develop and optimize highly efficient arid economical synthetic routs towards novel biologically active indole substances. In this regard, asymmetric synthesis is one of the most promising approaches for accessing enantio-pure compounds, including diverse indole derivatives.

Glucosidases are also involved in several important biological processes, such as the synthesis of glycoproteins and the lysosomal catabolism of glycol conjugates. In addition, α-glucosidase inhibitors have been also used as inhibitors of tumor metastasis, and as anti-obesity drugs, fungi static compounds, insect's anti-feedants, anti-viral and immune modulators. The inhibition of α-glucosidase is reported mainly to overcome the risk of postprandial hyperglycemia in diabetic patients, which in turn is associated with cardio-vascular and other health disorders. 1-Deoxynojirimycin, acarbose, miglitol, etc. have been developed as α-glucosidase inhibitors. However, many of them have adverse effects and low patient tolerability. Therefore, there is an urgent need for safe and effective α-glucosidase inhibitors to control diabetic and cardiovascular complications due to hyperglycemia.

Thus, novel α-glucosidase inhibitors incorporating an indole moiety solving the aforementioned problems is desired.

SUMMARY OF THE INVENTION

According to one aspect, there is provided novel α-glucosidase inhibitors incorporating an indole moiety, represented by Formula 1
Formula 1

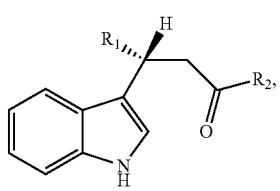

Wherein:
$R_1$ is thiophene, 2, 4-di chloro phenyl, 2, 6-di chloro phenyl, bromo phenyl, benzyl or nitrophenyl and $R_2$ is an aryl group or stereoisomers or pharmaceutically acceptable salts thereof.

Additionally, a method for preparing the α-glucosidase inhibitors of Formula 1 includes:
(a) Mixing a solution of $Cu(OTf)_2$ and a ligand in dry acetonitrile under an inert atmosphere to form a first mixture;
(b) Adding to the first mixture a solution of indole and a conjugated ketone in dry acetonitrile to form a reaction mixture;
(c) Stirring the reaction mixture at ambient temperature for about 24 hours to about 48 hours.
(d) Removing a solvent from the reaction mixture in vacuo.
(e) Extracting the mixture using an organic solvent, washing with brine and drying over $MgSO_4$.

The compounds represented by Formula I are useful in treating or preventing disorders related to postprandial hyperglycemia in diabetic patients and associated complications of diabetes such as microvascular complications (e.g., retinopathy, neuropathy, nephropathy and delayed wound healing).

These and other features of the present invention will become readily apparent upon further review of the following specification and drawings.

BRIEF DESCRIPTION OF THE DRAWINGS

The sole drawing FIGURE shows a schematic representation of the synthesis of indole derivatives (Compounds 3a-r), according to the present invention.

DETAILED DESCRIPTION OF THE PREFERRED EMBODIMENTS

Novel α-glucosidase inhibitors include propanone-substituted indole ring containing compounds of Formula I shown below.

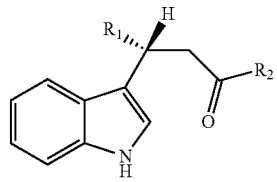

Formula I

Where in
$R_1$ is thiophene, 2, 4-di chloro phenyl, 2, 6-di chloro phenyl, bromo phenyl, methyl benzene or nitrophenyl and $R_2$ is an aryl groups or stereoisomers or pharmaceutically acceptable salts thereof.

The present inventors have evaluated the in vitro α-glucosidase inhibitory activity of the propanone-substituted indole ring containing compounds of Formula I as well as other propanone-substituted indole ring containing compounds. The present inventors have found that propanone-substituted indole ring containing compounds represented generally by Formula II (shown below) exhibit in vitro α-glucosidase inhibitory activity. The compounds represented by Formula II include compounds having the following chemical formula:

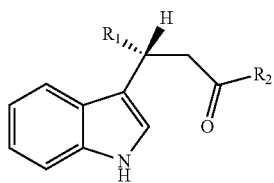

Formula II

Where in

R₁ and R₂ are independently selected from the group consisting of a phenyl group, a benzyl group, a thiophene group, and a naphthyl group, and are unsubstituted or substituted with one or more substituents selected from a halogen, straight or branched chain alkyl group having 1 to 3 carbon atoms, alkoxy, nitro, or hydroxyl group or stereoisomers or pharmaceutically acceptable salts thereof.

It should be noted that Formula I compounds fall within the definition of Formula II compounds. The particular compounds of Formula I and/or Formula II synthesized and evaluated for in vitro α-glucosidase inhibitory activity are listed in Table 1 below.

TABLE 1

Compounds 3a-r

| Compound | R₁ | R₂ |
| --- | --- | --- |
| 3a | phenyl | phenyl |
| 3b | 4-Cl-phenyl | naphthyl |
| 3c | 3,5-dimethylphenyl | phenyl |
| 3d | 4-methylphenyl | phenyl |
| 3e | 4-methoxyphenyl | phenyl |
| 3f | 4-Cl-phenyl | naphthyl |
| 3g | phenyl | naphthyl |
| 3h | 4-Cl-phenyl | phenyl |
| 3i | 3,5-dimethylphenyl | naphthyl |
| 3j | 4-methylphenyl | naphthyl |
| 3k | thiophene | phenyl |
| 3l | 3,5-dichlorophenyl | phenyl |
| 3m | 3,5-dichlorophenyl | phenyl |
| 3n | 4-methylphenyl | phenyl |
| 3o | thiophene | naphthyl |
| 3p | 4-nitrophenyl | phenyl |
| 3q | 4-bromophenyl | phenyl |
| 3r | 3-bromophenyl | phenyl |

The α-glucosidase inhibitors listed in Table 1 (Compounds 3a-3r) were prepared in moderate to good chemical yields with excellent enantioselectivity (up to 99.9%). These compounds 3a-r were identified as potent α-glucosidase enzyme inhibitors. All of these compounds were found to be several folds more active than the standard drug acarbose in in vitro biochemical assay.

β-Glucuronidase is a lysosomal enzyme that cleaves β-glucuronic acid linkages from the non-reducing termini of glycosaminoglycans, such as chondroitin sulfate, heparin sulfate, and hyaluronic acid. α-Glucosidase is a small intestinal membrane bound enzyme that catalyzes the hydrolysis of disaccharides to absorbable monosaccharide, i.e., glucose, and thus suppress the postprandial hyperglycemia. Inhibition of α-glucosidase can effectively overcome the risk of postprandial hyperglycemia, an independent risk factor of cardiovascular diseases.

All of the synthesized compounds 3a-r were evaluated for their in vitro α-glucosidase enzyme inhibition activity. The series compounds 3a-r exhibited a potent α-glucosidase inhibition with $IC_{50}$ values 43.3±0.92, 17.6±0.98, 25.2±1.96, 24.0±4.0, 27.1±0.69, 15.2±0.58, 43.9±0.51, 37.9±0.86, 15.1±0.4, 18.1±1.90, 21.8±0.25, 15.6±0.17, 4.3±0.13, 26.3±0.48, 11.8±0.06, 34.6±1.55, 24.9±1.61, and 33.2±0.75 µM, respectively. All tested compounds were found to be several fold more active than the standard drug, acarbose ($IC_{50}$=840±1.73 µM). Compound 3g having 3-naphthyl-1-phenylpropan-1-one moiety attached to indole ring, was found to be the least active in the series with $IC_{50}$ value 43.9±0.51 µM. However the activity increased when the phenyl ring of 1,3-diphenylpropan-1-one moiety was substituted with chloro atoms, as observed in compounds 3m ($IC_{50}$=4.3±0.13 µM) and 3l ($IC_{50}$=15.6±0.17 µM).

The substitution of the same phenyl ring with electron donating methoxy substituent also contributed in increasing the activity of compound 3e ($IC_{50}$=27.1±0.69 µM). Compounds 3b and 3f were found to be the most potent α-glucosidase inhibitors of the series with the $IC_{50}$ values 17.6±0.98 and 15.2±0.58 µM, respectively. The activity seems to be due to the presence of a naphthalene ring attached to the propan-1-one moiety, in place of phenyl. The comparison of activities of compounds 3e ($IC_{50}$=27.1±0.69 µM) and 3f ($IC_{50}$=15.2±0.78 µM) further support the initial inference that naphthalene moiety contributes more in the activity. The results are summarized in Table-2.

TABLE 2

Results of α-glucosidase inhibition assay on compounds 3a-r

| Compounds | α-Glucosidase Inhibition ($IC_{50}$ in µM) |
| --- | --- |
| 3a | 43.3 ± 0.92 |
| 3b | 17.6 ± 0.98 |
| 3c | 25.2 ± 1.96 |
| 3d | 24.0 ± 4.0 |
| 3e | 27.1 ± 0.69 |
| 3f | 15.2 ± 0.58 |
| 3g | 43.9 ± 0.51 |
| 3h | 37.9 ± 0.86 |
| 3i | 15.1 ± 0.4 |
| 3j | 18.1 ± 1.90 |
| 3k | 21.8 ± 0.25 |
| 3l | 15.6 ± 0.17 |
| 3m | 4.3 ± 0.13 |
| 3n | 26.3 ± 0.48 |
| 3o | 11.8 ± 0.06 |
| 3p | 34.6 ± 1.55 |
| 3q | 24.9 ± 1.61 |
| 3r | 33.2 ± 0.75 |
| Std. | Acarbose 840 ± 1.73 |

The present compounds can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating postprandial hyperglycemia in diabetic patients is an amount effective to inhibit α-glucosidase activity and less than an amount which causes toxicity in a patient.

A typical synthetic strategy was employed to obtain the title compounds 3a-r in moderate to good yields (22-89%) with excellent enantioselectivities up to 99.9% ee, as presented in FIG. 1. In the present investigation, the chiral Lewis acid catalysts, prepared from oxazoline-imidazoline-type ligands (L) and Cu(OTf)$_2$ as metal salt, was used. This modified ligand catalyst was employed in the asymmetric catalytic Friedel-Crafts alkylation of indole1 with enones (Z)-(2a-r) to afford the product (S)-3-(1H-indol-3-yl)propan-1-ones (3a-r). Eighteen derivatives were prepared using the optimized conditions which described in our earlier publications. The absolute configuration of the products 3a-r were assigned as (S) by optical correlation with those reported in the literature.

Referring to the sole drawing FIGURE, the synthetic strategy is as follows. A solution of Cu(OTf)$_2$ (15 mg, 0.042 mmol, 20 mol %) and chiral ligand L (17 mg, 0.042 mmol, 10 mol %) in dry CH$_3$CN (2 mL) is stirred for 1 hour at room temperature under argon atmosphere. To the resulting blue-green solution, a solution of indole (1) (50 mg, 0.425 mmol) and conjugated ketones (Compounds 2a-r) (0.425 mmol) in dry CH$_3$CN (1 mL) is added via syringe. The reaction mixture is then stirred at ambient temperature for 24-48 hours. The reaction is monitored by TLC until the starting material is completely consumed, then the solvent is removed under vacuum. Water (10 mL) is added and the mixture is extracted with EtOAc (2×25 mL), washed with brine (10 mL), and dried over MgSO$_4$. The product can be purified by column chromatography.

The Lewis acid-catalyzed enantioselective Friedel-Crafts alkylation of prochiral α,β-unsaturated enones are the key precursors towards the synthesis of various classes of compounds, including indole containing enone moieties. Their building blocks provide important and straightforward strategies to access structurally elaborated and optically pure molecules. It is envisaged that the novel pharmacophore as represented by the reaction in FIG. 1 would generate novel molecular entities, which are likely to exhibit interesting biological properties in animal models.

The newly synthesized α-glucosidase inhibitors may be utilized by medicinal chemists as structural templates to further improve biological activities. The potent α-glucosidase inhibiting activities of these compounds indicate their potential as possible drug candidates for the treatment of hyperglycemia and associated diabetic and cardiovascular complications and related health disorders. Thus, the discovery of new indole derivatives as α-glucosidase inhibitors can open up new vistas for further research in this important field as this enzyme is actively involved in the on-set of diabetic, and cardiovascular complications.

The following examples will further illustrate the synthetic processes of making the enantiomerically pure indole derivatives 3a-r via Friedel-Crafts alkylation of indole 1 with enones 2a-r.

EXAMPLE 1

Assay Protocol for α-Glucosidase Inhibition (In Vitro α-Glucosidase Inhibition Assay)

α-Glucosidase inhibition assay was performed spectrophotometrically. α-Glucosidase from *Saccharomyces cervi-* siae was dissolved in phosphate buffer (pH 6.8, 50 mM). Test compounds were dissolved in 70% DMSO. In 96-well plates, 20 μL of test sample, 20 μL of enzyme and 135 μL of buffer were added and incubated for 15 minutes at 37° C. After incubation, 25 μL, of p-nitrophenyl-α-D-glucopyranoside (0.7 mM, Sigma Aldrich) was added and the change in absorbance was monitored for 30 minutes at 400 nm. Test compound was replaced by DMSO (7.5% final) as control. Acarbose (Acarbose, Sigma Aldrich) was used as a standard inhibitor.

The products were isolated in a moderate to excellent yields (up to 89%) with excellent enantioselectivities (up to 99.9%). These compounds 3a-r were evaluated for their in vitro α-glucosidase inhibitory activity and found to be potent inhibitors as discussed infra.

EXAMPLE 2

Synthesis of (S)-4-Isopropyl-2-(3-((S)-4-isopropyl-1-(4-methoxyphenyl)-4,5-dihydro-1H-imidazol-2-yl)pentan-3-yl)-4,5-dihydrooxazole (L)

The ligand L was prepared by following the procedure described by Barakat et al. "Highly Enantioselective Friedel-Crafts alkylations of Indoles with α,β-unsaturated Ketones under Cu(II)-simple Oxazoline-Imidazoline Catalysts," *Tetrahedron*, 69: 5185-5192, 2013. The product L was obtained as slightly yellowish colored oily product (470 mg, 58.9%). $^1$H-NMR (CDCl$_3$, 400 MHz) δ 0.71-0.99 (m, 18H, 2CH$_3$CH$_2$ &2(CH$_3$)$_2$CH), 1.59-1.72 (m, 1H, (CH$_3$)$_2$CH, imidazole), 1.73-1.85 (m, 1H, (CH$_3$)$_2$CH, oxazole), 1.85-2.10 (m, 4H, CH$_3$CH$_2$), 3.38-3.50 (m, 2H, NCH$_2$CH, imidazole), 3.58-3.72 (m, 1H, OCH$_{2(a)}$CH, oxazole), 3.72-3.77 (m, 1H, OCH$_{2(b)}$CH, oxazole), 3.79 (s, 3H, ArOCH$_3$), 3.87-3.96 (m, 1H, NCH$_2$CH(CH$_3$)$_2$, imidazole), 4.06-4.19 (m, 1H, OCH$_2$CH(CH$_3$)$_2$, oxazole), 6.80 (d, 2H, J=8.8 Hz, ArH) and 7.06 (d, 2H, J=8.8 Hz, ArH). The other analytical data are in accordance with the literature.

EXAMPLE 3

Preparation of (S)-3 (1H-Indol-3-yl)-1,3-diphenyl-propan-1-one (3a)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and chalcone 2a (89 mg, 0.425 mmol) in CH$_3$CN (3 mL) were reacted according to GP1. Purification by chromatography on silica gel column (EtOAc/hexanes 1:9) yielded compound 3a as a white solid (119 mg, 86%). This was identified as a known compound on the basis of spectral comparison. Enantiomeric excess was determined by chiral HPLC (Chiracel OD-H column), hexanes: i-PrOH 80:20, 0.4 mL/min, λ=220 nm, t$_r$(minor)=8.73 min, t$_r$(major)=9.68 min, to be 99.92%; m.p. 147-149° C., [α]$^{25}_D$=+29.6 (c, 0.45, CHCl$_3$) [lit. [23a] m.p. 148-152° C., [α]$^{25}_D$+25.3 (c, 0.3, CHCl$_3$)]; [Anal. calcd. for C$_{23}$H$_{19}$NO: C, 84.89; H, 5.89; N, 4.30; Found C, 85.17; H, 5.63; N, 4.42]; IR (cm$^{-1}$): 3413, 1679, 1597, 1451, 745, 698; $^1$H-NMR (CDCl$_3$, 400 MHz) δ 3.73-3.80 (m, 2H, COCH$_2$), 5.07 (t, 1H, J=6.6 Hz, ArCHCH$_2$), 6.99 (s, 1H, CHNH), 7.25-7.44 (m, 11H, ArH), 7.92 (d, 1H, J=7.3 Hz, 1H of 4H-indole & 2H of COPhH$_{ortho}$), 7.96 (s, 1H, NH of Indole); $^{13}$C-NMR (CDCl$_3$, 100 MHz): δ 38.29, 45.28, 111.18, 119.4, 119.5, 119.6, 121.5, 122.2, 126.4, 126.5, 127.9, 128.2, 128.5, 128.7, 133.1, 136.6, 137.1, 144.3, 198.62; LC/MS (ESI): M$^+$, found m/z 325.15, C$_{23}$H$_{19}$NO requires 325.15.

EXAMPLE 4

Preparation of (S)-3-(4-Chlorophenyl)-3-(1H-indol-3-yl)-1-(naphthalen-2-yl)propan-1-one (3b)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2b (124 mg, 0.425 mmol) in CH$_3$CN (3 mL) were reacted according to GP2. Purification by chromatography on silica (EtOAc/hexane 1:9) yielded compound 3b as a light yellow solid (141 mg, 81%). Enantiomeric excess was determined by chiral HPLC (Chiracel OD-H column), hexane:i-PrOH 80:20, 0.4 mL/min, λ=220 nm, t$_r$(minor)=8.80 min, t$_r$(major)=9.73 min, to be 95.6%; m.p. 237-241° C., [α]$_D^{25}$=+19.1 (c, 0.45, CHCl$_3$); [Anal. calcd. for C$_{27}$H$_{20}$ClNO: C, 79.11; H, 4.92; N, 3.42; Found C, 79.35; H, 5.02; N, 3.59]. IR (KBr): 3409, 2923, 1677, 815, 744, 476 cm$^{-1}$; $^1$H-NMR (CDCl$_3$, 400 MHz) δ 3.75-3.86 (m, 1H, COCH$_{2(a)}$), 3.86-3.98 (m, 1H, COCH$_{2(b)}$), 5.09 (t, 1H, J=7.3 Hz, ArCHCH$_2$), 7.01-7.07 (m, 2H, ArH), 7.14-7.38 (m, 7H, ArH), 7.38-7.46 (m, 1H, ArH), 7.48-7.66 (m, 2H, ArH), 7.83-7.91 (m, 2H, ArH), 7.91-7.99 (m, 2H, ArH), 8.42 (s, 1H, NH of Indole); $^{13}$C-NMR (CDCl$_3$, 100 MHz): δ 28.5, 45.0, 111.1, 119.0, 119.5, 121.1, 122.0, 123.9, 124.6, 126.5, 128.1, 128.2, 128.6, 128.7, 129.3, 132.0, 133.8, 134.1, 135.2, 136.7, 137.0, 139.8, 142.7, 199.9; LC/MS (ESI): M$^+$, found m/z 409.09, C$_{27}$H$_{20}$ClNO requires 409.12.

EXAMPLE 5

Preparation of (S)-3-(1H-Indol-3-yl)-3-mesityl-1-phenylpropan-1-one (3c)

Oxazoline-imidazoline ligand L (25 mg, 15 mol %), Cu(OTf)$_2$ (22 mg, 30 mol %), indole (50 mg, 0.425 mmol) and enone 2c (107 mg, 0.425 mmol) in CH$_3$CN (3 mL) were reacted according to GP2. Purification by chromatography on silica gel column (EtOAc/hexanes 1:9) yielded compound 3c as a light yellow solid (63 mg, 40%). Enantiomeric excess was determined by chiral HPLC (Chiracel OD-H), hexane:i-PrOH 80:20, 0.4 mL/min, λ=220 nm, t$_r$(minor)=18.9 min, t$_r$(major)=23.0 min, to be 96%; m.p. 169-171° C., [α]$_D^{25}$=+11.5 (c, 0.45, CHCl$_3$); [Anal. calcd. for C$_{26}$H$_{25}$NO: C, 84.98; H, 6.86; N, 3.81; found C, 85.11; H, 6.73; N, 3.75]. IR (KBr): 3409, 2921, 1677, 1451, 744, 690 cm$^{-1}$; $^1$H-NMR (CDCl$_3$, 400 MHz) δ 2.27 (s, 9H, ArCH$_3$), 3.57-3.63 (m, 1H, COCH$_{2(a)}$), 4.05-4.12 (m, 1H, COCH$_{2(a)}$), 5.49 (t, 1H, J=6.6 Hz, ArCHCH$_2$), 6.81 (s, 2H, Me$_3$PhH), 6.85-6.94 (m, 1H, ArH), 6.94-7.02 (m, 1H, ArH), 7.02-7.15 (m, 1H, ArH), 7.20-7.36 (m, 2H, ArH), 7.41-7.50 (m, 2H, ArH), 7.50-7.59 (m, 1H, ArH), 7.90 (s, 1H, NH of Indole), 7.98 (d, J=7.3 Hz, 2H, ArH$_{ortho}$); $^{13}$C-NMR (CDCl$_3$, 100 MHz): δ 20.9, 21.4, 29.8, 33.2, 43.0, 111.09, 117.8, 118.7, 119.1, 119.9, 121.7, 122.1, 127.0, 128.2, 128.3, 128.8, 130.0, 138.8, 136.8, 137.2, 137.3, 199.24; LC/MS (ESI): M$^+$, found m/z 367.17, C$_{26}$H$_{25}$NO requires 367.19.

EXAMPLE 6

Preparation of (S)-3-(1H-Indol-3-yl)-1-phenyl-3-(p-tolyl)propan-1-one (3d)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2d (95 mg, 0.425 mmol) in CH$_3$CN (3 mL) were reacted according to GP1. Purification by chromatography on silica gel column (EtOAc/hexanes 1:9) yielded compound 3d as yellow solid (105 mg, 73%). Enantiomeric excess was determined by chiral HPLC (Chiracel OD-H), hexanes:i-PrOH 80:20, 0.4 mL/min, λ=220 nm, tr(minor)=27.3 min, tr(major)=31.2 min, to be 95.8%; m.p. 153-155° C., [α]$^D_{25}$=+14.6 (c, 0.45, CHCl$_3$ [Anal. calcd. for C$_{24}$H$_{21}$NO: C, 84.92; H, 6.24; N, 4.13; Found C, 84.66; H, 6.15; N, 3.97]. IR (KBr): 3413, 1680, 1452, 743, 689 cm$^{-1}$; $^1$H-NMR (CDCl$_3$, 400 MHz) δ 2.26 (s, 3H, ArCH$_3$), 3.65-3.78 (m, 1H, COCH$_{2(a)}$), 3.78-3.89 (m, 1H, COCH$_{2(b)}$), 5.02 (t, 1H, J=7.4 Hz, ArCHCH$_2$), 6.98-7.61 (m, 12H, ArH), 7.89 (s, 1H, NH of Indole), 7.93 (d, J=7.3 Hz, 2H of COPhH$_{ortho}$); $^{13}$C-NMR (CDCl$_3$, 100 MHz): δ 21.1 (ArCH$_3$), 37.9 (ArCHCH$_2$), 45.4 (ArCHCH$_2$), 111.2, 119.4, 119.5, 119.6, 121.6, 122.2, 126.9, 127.8, 128.2, 128.7, 129.4, 133.3, 135.8, 136.7, 137.1, 141.3, 198.71; LC/MS (ESI): M$^+$, found m/z 339.19, C$_{24}$H$_{21}$NO requires 339.16.

EXAMPLE 7

Preparation of (S)-3-(1H-Indol-3-yl)-3-(4-methoxyphenyl)-1-phenylpropan-1-one (3e)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2e (101 mg, 0.425 mmol) in CH$_3$CN (3 mL) were reacted according to GP1. Purification by chromatography on silica gel column (EtOAc/hexane 1:9) yielded compound 3e as a yellow solid (134 mg, 89%). Enantiomeric excess was determined by HPLC (Chiracel OD-H), hexanes:i-PrOH 80:20, 0.4 mL/min, λ=220 nm, tr(minor)=20.1 min, tr(major)=24.0 min, to be 96.4%; m.p. 134-136° C., [α]$_D^{25}$=+21.4 (c, 0.45, CHCl$_3$); [Anal, calcd. for C$_{24}$H$_{21}$NO$_2$: C, 81.10; H, 5.96; N, 3.94; Found C, 80.79; H, 5.86; N, 4.07]. IR (KBr): 3412, 2923, 1674, 1509, 1245, 1177, 746, 476 cm$^{-1}$; $^1$H-NMR (CDCl$_3$, 400 MHz) δ 3.73 (s, 3H, ArOCH$_3$), 3.77-3.85 (m, 1H, COCH$_{2(a)}$), 3.85-3.98 (m, 1H, COCH$_{(b)}$), 5.06 (t, 1H, J=7.4 Hz, ArCHCH$_2$), 6.78-7.83 (m, 2H, ArH), 6.97-7.05 (m, 2H, ArH), 7.11-7.19 (m, 1H, ArH), 7.22-7.62 (m, 6H, ArH), 7.84-8.01 (m, 3H, ArH), 8.42 (s, 1H, NH of Indole); $^{13}$C-NMR (CDCl$_3$, 100 MHz): δ 37.8, 45.5, 55.3, 111.3, 113.9, 119.7, 121.5, 122.0, 124.0, 126.8, 127.8, 128.5, 128.8, 129.6, 132.4, 134.9, 135.8, 136.7, 158.1, 198.8; LC/MS (ESI): M$^+$, found m/z 355.19, C$_{24}$H$_{21}$NO$_2$ requires 355.16.

EXAMPLE 8

Preparation of (S)-3-(1H-Indol-3-yl)-3-(4-methoxyphenyl)-1-(naphthalen-2-yl)propan-1-one (3f)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2f (123 mg, 0.425 mmol) in CH$_3$CN (3 mL) were reacted according to GP1. Purification by chromatography on silica gel column (EtOAc/hexanes 1:9) yielded compound 3f as an off white solid (112 mg, 66%). Enantiomeric excess was determined by chiral HPLC (Chiracel OD-H), hexane:i-PrOH 80:20, 0.4 mL/min, λ=220 nm, tr(major)=39.4 min, tr(minor)=49.1 min, to be 90.8%; m.p. 159-162° C., [α]$^{25}_D$=+17.5 (c, 0.45, CHCl$_3$); [Anal. calcd. for C$_{28}$H$_{23}$NO$_2$: C, 82.94; H, 5.72; N, 3.45; Found C, 83.22; H, 5.61; N, 3.73]. IR (KBr): 3413, 3007, 2930, 1679, 1610, 1509, 1246, 1177, 1032, 745, 544 cm$^{-1}$; $^1$H-NMR (CDCl$_3$, 400 MHz) δ 3.65-3.82 (m, 2H+3H, COCH$_2$ & ArOCH$_3$), 5.01 (t, 1H, J=7.3 Hz, ArCHCH$_2$), 6.75-6.83 (m, 2H, ArH), 6.97-7.07 (m, 2H, ArH), 7.11-7.20 (m, 1H, ArH), 7.21-7.48 (m, 8H, ArH), 7.49-7.56 (m, 1H, ArH), 7.91 (s, 1H, NH of Indole), 7.93 (s, 2H. ArH); $^{13}$C-NMR (CDCl$_3$, 100 MHz): δ 37.5, 45.5, 55.3, 111.4, 113.8, 116.2, 118.1, 119.7, 119.9, 121.6, 122.1, 123.4, 126.7, 127.0, 128.3, 128.9, 130.1, 130.4, 131.9, 133.3, 135.2, 136.4, 136.7, 137.2, 158.0, 198.8; LC/MS (ESI): M$^+$, found m/z 405.18, C$_{28}$H$_{23}$NO$_2$ requires 405.17.

EXAMPLE 9

Preparation of (S)-3-(1H-Indol-3-yl)-1-(naphthalen-2-yl)-3-phenylpropan-1-one (3g)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2g (110 mg, 0.425 mmol) in CH$_3$CN (3 mL) were reacted according to GP1. Purification by chromatography on silica (EtOAc/hexane 1:9) yielded compound 3g as a white solid (75 mg, 47%). Enantiomeric excess was determined by chiral HPLC (Chiracel OD-H), hexane:i-PrOH 80:20, 0.4 mL/min, λ=220 nm, t$_r$(minor)=12.0 min, t$_r$(major)=14.9 min, to be 95.5%; m.p. 166-169° C., [α]$_D^{25}$+24.2 (c, 0.45, CHCl$_3$); [Anal. calcd. for C$_{27}$H$_{21}$NO: C, 86.37; H, 5.64; N, 3.73. Found C, 85.98; H, 5.87; N, 3.93]. IR (KBr): 3415, 1677, 1597, 1456, 746, 476 cm$^{-1}$; $^1$H-NMR (CDCl$_3$, 400 MHz) δ 3.83-3.91 (m, 1H, COCH$_{2(a)}$), 3.91-3.95 (m, 1H, COCH$_{2(b)}$), 5.13 (t, 1H, J=7.3 Hz, ArCHCH$_2$), 7.00-7.11 (m, 3H, ArH), 7.11-7.23 (m, 2H, ArH), 7.23-7.50 (m, 6H, ArH), 7.50-7.63 (m, 2H, ArH), 7.95-8.19 (m, 4H, ArH), 8.43 (s, 1H, NH of Indole); $^{13}$C-NMR (CDCl$_3$, 100 MHz): δ 38.3, 45.3, 111.2, 116.0, 119.4, 119.5, 119.6, 121.5, 122.2, 123.3, 125.1, 126.4, 126.6, 127.9, 128.2, 128.5, 128.7, 129.4, 131.0, 133.0, 136.5, 137.1, 141.1, 144.3, 198.6; LC/MS (ESI): M$^+$, found 375.15, C$_{27}$H$_{21}$NO requires 375.16.

EXAMPLE 10

Preparation of (S)-3-(4-Chlorophenyl)-3-(1H-indol-3-yl)-1-phenylpropan-1-one (3h)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2h (103 mg, 0.425 mmol) in CH$_3$CN (3 mL) were reacted according to GP1. Purification by chromatography on silica (EtOAc/hexane 1:9, R$_f$=0.75) yielded compound 3h as a light yellow solid (128.5 mg, 84%). Enantiomeric excess was determined by chiral HPLC (Chiracel OD-H column), hexane:i-PrOH 80:20, 0.4 mL/min, λ=220 nm, t$_r$(minor), =8.84 min, t$_r$(major)=9.74 min, to be 93.85%; m.p. 189-192° C., [α]$^{25}_D$=+23.7 (c, 0.45, CHCl$_3$); [Anal. calcd. for C$_{23}$H$_{18}$ClNO: C, 76.77; H, 5.04; N, 3.89; Found C, 76.92; H, 5.12; N, 3.71]. IR (cm$^{-1}$): 3369, 1677, 745, 582, 502; $^1$H-NMR (CDCl$_3$, 400 MHz) δ 3.64-3.38 (m, 2H, COCH$_2$), 5.04 (t, 1H, J=7.3 Hz, ArCHCH$_2$), 6.93-7.11 (m, 2H, ArH & 1H of NCH of indole), 7.12-7.63 (m, 8H, ArH), 7.92 (d, J=7.3 Hz, 1H of 4H-indole & 2H of COPhH$_{ortho}$), 7.99 (s, NH of Indole); $^{13}$C-NMR (CDCl$_3$, 100 MHz): δ 29.8, 45.0, 113.3, 119.0, 119.9, 121.2, 123.3, 126.5, 128.1, 128.2, 128.6, 128.7, 132.0, 133.8, 136.7, 137.0, 140.0, 142.8, 198.3; LC/MS (ESI): M$^+$, found 359.10, C$_{23}$H$_{18}$ClNO requires 359.11.

EXAMPLE 11

Preparation of (S)-3-(1H-Indol-3-yl)-3-mesityl-1-(naphthalen-2-yl)propan-1-one (3i)

Oxazoline-imidazoline ligand L (34 mg, 20 mol %), Cu(OTf)$_2$ (22 mg, 30 mol %), indole (50 mg, 0.425 mmol) and enone 2i (129 mg, 0.425 mmol) in CH$_3$CN (3 mL) were reacted according to GP2. Purification by chromatography on silica (EtOAc/hexane 1:9) yielded compound 3i as a yellow solid (39 mg, 22%). Enantiomeric excess was determined by chiral HPLC (Chiracel OD-H), hexane:i-PrOH 80:20, 0.4 mL/min, λ=220 nm, t$_r$(minor)=18.8 min, t$_r$(major)=22.9 min, to be 97.8%; m.p. 227-229° C., $[\alpha]_D^{25}$=+17.3 (c, 0.45, CHCl$_3$); [Anal. calcd. for C$_{30}$H$_{27}$NO: C, 86.30; H, 6.52; N, 3.35; Found C, 86.19; H, 6.61; N, 3.49]. IR (KBr): 3410, 3319, 2652, 1653, 1619, 1590, 1457, 744 cm$^{-1}$; $^1$H-NMR (CDCl$_3$, 400 MHz) δ 2.27 (s, 9H, ArCH$_3$), 3.68-3.78 (m, 1H, COCH$_{2(a)}$), 4.17-4.23 (m, 1H, COCH$_{2(b)}$), 5.54 (t, 1H, J=6.6 Hz, ArCHCH$_2$), 6.79-6.92 (m, 3H, ArH), 7.92-7.20 (m, 2H, ArH), 7.20-7.38 (m, 3H, ArH), 7.50-7.68 (m, 2H, ArH), 7.84-7.98 (m, 3H, ArH), 8.05-8.08 (m, 1H, ArH), 8.47 (s, 1H, NH of Indole); $^{13}$C-NMR (CDCl$_3$, 100 MHz): δ 21.4, 21.5, 29.8, 33.4, 43.0, 111.0, 115.8, 116.2, 117.6, 119.1, 119.3, 120.0, 121.5, 122.0, 123.2, 124.1, 125.5, 127.1, 128.0, 128.5, 129.6, 131.0, 132.8, 134.6, 135.9, 137.0, 137.3, 199.1; LC/MS (ESI): M$^+$, found 417.22, C$_{30}$H$_{27}$NO requires 417.21.

EXAMPLE 12

Preparation of (S)-3-(1H-Indol-3-yl)-1-(naphthalen-2-yl)-3-(p-tolyl)propan-1-one (3j)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2j (116 mg, 0.425 mmol) in CH$_3$CN (3 mL) were reacted according to GP1. Purification by chromatography on silica (EtOAc/hexane 1:9) yielded compound 3j as a yellowish solid (45 mg, 27%). Enantiomeric excess was determined by chiral HPLC (Chiracel OD-H), hexane:i-PrOH 80:20, 0.4 mL/min, λ=220 nm, t$_r$(minor)=7.6 min, t$_r$(major)=9.7 min, to be 93.4%; m.p. 174-177° C., $[\alpha]_D^{25}$=+9.1 (c, 0.45, CHCl$_3$); [Anal. calcd. for C$_{28}$H$_{23}$NO: C, 86.34; H, 5.95; N, 3.60; Found C, 86.24; H, 6.09; N, 3.37]. IR (KBr): 3413, 2923, 2854, 1676, 1625, 1461, 816, 748, 476 cm$^{-1}$; $^1$H-NMR (CDCl$_3$, 400 MHz) δ 2.27 (s, 3H, ArCH$_3$), 3.76-3.88 (m, 1H, COCH$_{2(a)}$), 3.89-3.98 (m, 1H, COCH$_{2(b)}$), 5.08 (t, 1H, J=7.3 Hz, ArCHCH$_2$), 6.87-7.45 (m, 7H, ArH), 7.55-7.71 (m, 3H, ArH), 7.83-8.02 (m, 6H, ArH), 8.42 (s, 1H, NH of Indole); $^{13}$C-NMR (CDCl$_3$, 100 MHz): δ 21.1, 38.1, 45.4, 111.2, 116.1, 118.0, 119.5, 122.2, 123.8, 124.2, 125.8, 126.7, 127.8, 128.4, 129.2, 129.8, 132.2, 134.1, 135.9, 136.8, 138.2, 139, 8, 141.1, 197.8; LC/MS (ESI): M$^+$, found 389.18, C$_{28}$H$_{23}$NO requires 389.18.

EXAMPLE 13

Preparation of (R)-3-(1H-Indol-3-yl)-1-phenyl-3-(thiophen-2-yl)propan-1-one (3k)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2k (91 mg, 0.425 mmol) in CH$_3$CN (3 mL) were reacted according to GP2. Purification by chromatography on silica (EtOAc/hexane 1:9) yielded compound 3k as a white solid (91 mg, 65%). Enantiomeric excess was determined by chiral HPLC (Chiracel OD-H), hexane:i-PrOH 80:20, 0.4 mL/min, λ=220 nm, t$_r$(minor)=3.1 min, t$_r$(major)=8.6 min, to be 89.8%; m.p. 112-115° C., $[\alpha]_D^{25}$=+6.3 (c, 0.45, CHCl$_3$); [Anal. calcd. for C$_{21}$H$_{17}$NOS: C, 76.10; H, 5.17; N, 4.23; Found C, 75.89; H, 5.31; N, 4.43]. IR (KBr): 3419, 1676, 1594, 1456, 741, 576 cm$^{-1}$; $^1$H-NMR (CDCl$_3$, 400 MHz) δ 3.84 (t, J=6.6 Hz, 2H, COCH$_2$), 5.37 (t, 1H, J=6.6 Hz, ArCHCH$_2$), 6.85-6.98 (m, 2H, ArH), 7.02-8.65, (m, 9H, ArH), 7.92-7.94 (m, 2H, ArH), 7.99 (s, NH of Indole); $^{13}$C-NMR (CDCl$_3$, 100 MHz): δ 33.6, 46.2, 111.3, 116.1, 119.5, 119.6, 121.9, 122.3, 123.5, 124.3, 126.6, 128.2, 128.7, 133.2, 136.0, 136.4, 143.9, 148.8, 198.1; LC/MS (ESI): M$^+$, found 331.11, C$_{21}$H$_{17}$NOS requires 331.10.

EXAMPLE 14

Preparation of 3-(2,4-dichlorophenyl)-3-(1H-indol-3-yl)-1-phenylpropan-1-one (3l)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2l (117 mg, 0.425 mmol) in CH$_3$CN (3 mL) were reacted according to GP2. Purification by chromatography on silica gel column (EtOAc/hexanes 1:9) yielded compound 3l as an off-white solid (141 mg, 84%). Enantiomeric excess was determined by chiral HPLC (Chiracel OD-H), hexane:i-PrOH 80:20, 0.4 mL/min, λ=220 nm, t$_r$(major)=8.3 min, t$_r$(major)=9.7 min, to be 97.5%; m.p. 110-112° C., $[\alpha]_D^{25}$=+8.7 (c, 0.45, CHCl$_3$); [Anal. calcd. for C$_{23}$H$_{17}$ClNO: C, 70.06; H, 4.35; N, 3.55; Found C, 69.91; H, 4.29; N, 3.43]. IR (KBr): 3380, 2945, 1676, 1501, 1165, 1053, 745, 572 cm$^{-1}$; $^1$H-NMR (CDCl$_3$, 400 MHz) δ 3.71 & 3.74 (dd, 1H, J=14.0 Hz, 5.6 Hz, COCH$_{2(a)}$), 3.97 & 4.01 (dd, 1H, J=14.0 Hz, 6.0 Hz, COCH$_{2(b)}$), 5.27 (t, 1H, J=5.6 Hz, ArCHCH$_2$), 6.90 (t, 1H, J=5.8 Hz, ArH), 7.02 (t, 1H, J=6.0 Hz, ArH), 7.26-7.31 (m, 3H, ArH), 7.38 (d, 1H, J=6.4 Hz, ArH), 7.44 (d, 1H, J=6.8 Hz, ArH), 7.50 (t, 2H, J=6.0 Hz, ArH), 7.54 (d, 1H, J=2.4 Hz, ArH), 7.62 (t, 1H, J=8.4 Hz, ArH), 7.99 (d, 2H, J=4.0 Hz, ArH$_{(orthoproton)}$), 10.91 (s, 1H, NH of Indole); $^{13}$C-NMR (CDCl$_3$, 100 MHz): δ 33.27, 43.72, 111.34, 116.23, 117.93, 118.60, 121.24, 123.12, 126.18, 127.38, 128.10, 128.22, 128.73, 128.91, 130.52, 131.15, 133.46, 136.34, 136.58, 141.51, 197.90; LC/MS (ESI): M$^+$, found m/z 393.10, C$_{23}$H$_{17}$ClNO requires 393.07.

EXAMPLE 15

Preparation of 3-(2,6-dichlorophenyl)-3-(1H-indol-3-yl)-1-phenylpropan-1-one (3m)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2m (117 mg, 0.425 mmol) in CH$_3$CN (3 mL) were reacted according to GP1. Purification by chromatography on silica gel column (EtOAc/hexanes 1:9) yielded compound 3m as an off-white solid (133 mg, 78%). Enantiomeric excess was determined by chiral HPLC (Chiracel OD-H), hexane:i-PrOH 80:20, 0.4 mL/min, λ=220 nm, t$_r$(minor)=8.3 min, t$_r$(major)=9.8 min, to be 81.7%; m.p. 119-121° C., $[\alpha]_D^{25}$=+1.7 (c, 0.45, CHCl$_3$); [Anal. calcd. for C$_{23}$H$_{17}$ClNO: C, 70.06; H, 4.35; N, 3.55; Found C, 70.13; H, 4.46; N, 3.29]. IR (KBr): 3409, 2927, 1681, 1519, 1248, 1029, 741, 567 cm$^{-1}$; $^1$H-NMR (CDCl$_3$, 400 MHz) δ 4.03 & 4.06 (dd, 1H, J=13.6 Hz, 6.0 Hz, COCH$_{2(a)}$), 4.24 & 4.28 (dd, 1H, J=14.0 Hz, 5.6 Hz, COCH$_{2(b)}$), 5.27 (t, 1H, J=6.0 Hz, ArCHCH$_2$), 6.81 (t, 1H, J=6.0 Hz, ArH), 6.98 (t, 1H, J=5.6 Hz, ArH), 7.11 (d, 1H, J=6.4 Hz, ArH), 7.21 (t, 2H, J=6.4 Hz, ArH), 7.30 (d, 1H, J=6.8 Hz, ArH), 7.32 (d, 1H, J=0.8 Hz, ArH), 7.52 (t, 3H, J=6.0 Hz, ArH), 7.63 (t, 1H, J=6.0 Hz, ArH), 7.99 (d, 2H, J=6.0 Hz, ArH$_{(orthoproton)}$), 10.92 (s, 1H, NH of Indole); $^{13}$C-NMR (CDCl$_3$, 100 MHz): δ 34.12, 41.85, 111.91, 113.67, 115.92, 118.49, 120.88, 123.94, 126.43, 128.04, 128.10, 128.85, 131.42, 131.95, 133.51, 136.24, 136.58, 138.36, 198.18; LC/MS (ESI): M$^+$, found m/z 393.10, C$_{23}$H$_{17}$ClNO requires 393.07.

EXAMPLE 16

Preparation of 3-(1H-indol-3-yl)-1-phenyl-3-(m-tolyl)propan-1-one (3n)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2n (94.5 mg, 0.425 mmol) in CH$_3$CN (3 mL) were reacted according to GP1. Purification by chromatography on silica gel column (EtOAc/hexanes 1:9) yielded compound 3n as an off-white solid (114 mg, 79%). Enantiomeric excess was determined by chiral HPLC (Chiracel OD-H), hexane:i-PrOH 80:20, 0.4 mL/min, λ=220 nm, t$_r$(minor)=9.1 min, t$_r$(major)=9.8 min, to be 72.4%; m.p. 130-132° C., [α]$^{25}_D$=+3.3 (c, 0.45, CHCl$_3$); [Anal. calcd. for C$_{24}$H$_{21}$NO: C, 84.92; H, 6.24; N, 4.13; Found C, 85.03; H, 6.11; N, 3.98]. IR (KBr): 3419, 1678, 1459, 1226, 1044, 741, 681 cm$^{-1}$; $^1$H-NMR (CDCl$_3$, 400 MHz) δ 2.20 (s, 3H, CH$_3$), 4.74 & 3.77 (dd, 1H, J=13.6 Hz, 6.0 Hz, COCH$_{2(a)}$), 3.88 & 3.92 (dd, 1H, J=14.0 Hz, 5.6 Hz, COCH$_{2(b)}$), 4.80 (t, 1H, J=6.0 Hz, ArCHCH$_2$), 6.88 (t, 2H, J=6.0 Hz, ArH), 6.99 (t, 1H, J=6.0 Hz, ArH), 7.08 (t, 1H, J=5.6 Hz, ArH), 7.17-7.19 (m, 2H, ArH), 7.27 (d, 1H, J=6.4 Hz, ArH), 7.30 (d, 1H, J=2.0 Hz, ArH), 7.40 (d, 1H, J=6.4 Hz, ArH), 7.49 (t, 2H, J=6.0 Hz, ArH), 7.60 (t, 1H, J=6.0 Hz, ArH), 7.99 (d, 2H, J=6.0 Hz, ArH$_{(orthoproton)}$), 10.89 (s, 1H, NH of Indole); $^{13}$C-NMR (CDCl$_3$, 100 MHz): δ 20.60, 37.61, 44.01, 11.31, 115.13, 118.21, 118.33, 119.95, 120.00, 126.39, 128.02, 128.09, 128.70, 130.52, 133.65, 134.71, 136.38, 136.90, 139.83, 138.43, 142.22, 198.49; LC/MS (ESI): M$^+$, found m/z 339.10, C$_{24}$H$_{21}$NO requires 339.16.

EXAMPLE 17

Preparation of 3-(1H-indol-3-yl)-1-(naphthalen-2-yl)-3-(thiophen-2-yl)propan-1-one (3o)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2o (112 mg, 0.425 mmol) in CH$_3$CN (3 mL) were reacted according to GP1. Purification by chromatography on silica gel column (EtOAc/hexanes 1:9) yielded compound 3o as an off-white solid (145 mg, 89%). Enantiomeric excess was determined by chiral HPLC (Chiracel OD-H), hexane:i-PrOH 80:20, 0.4 mL/min, λ=220 nm, t$_r$(major)=10.217 min, t$_r$(minor)=14.345 min, to be 93.2%; m.p. 111-112° C., [α]$^{25}_D$=+11.6 (c, 0.45, CHCl$_3$); [Anal. calcd. for C$_{25}$H$_{19}$NOS: C, 78.71; H, 5.02; N, 3.67; Found C, 79.01; H, 5.09; N, 3.51]. IR (KBr): 3410, 1675, 1585, 1445, 1183, 739, 579, cm$^{-1}$; $^1$H-NMR (CDCl$_3$, 400 MHz) δ 3.98-4.08 (m, 2H, COCH$_2$), 5.22 (t, 1H, J=6.0 Hz, ArCHCH$_2$), 6.86 (t, 2H, J=4.0 Hz, ArH), 6.93 (t, 1H, J=6.4 Hz, ArH), 6.99-7.05 (m, 2H, ArH), 7.21 & 7.22 (dd, 1H, J=4.0 Hz, 1.2 Hz, ArH), 7.31 (d, 1H, J=6.8 Hz, ArH), 7.34 (d, 1H, J=1.6 Hz, ArH), 7.50 (d, 1H, J=6.4 Hz, ArH), 7.59-7.66 (m, 2H, ArH), 7.94-7.99 (m, 2H, ArH), 8.11 (d, 1H, J=5.6 Hz, ArH), 8.77 (s, 1H, ArH), 10.87 (s, 1H, NH of Indole); $^{13}$C-NMR (CDCl$_3$, 100 MHz): δ 32.49, 45.32, 111.52, 114.43, 117.76, 118.49, 119.12, 121.08, 122.24, 123.63, 123.94, 126.02, 126.55, 127.10, 127.68, 128.31, 128.75, 129.81, 130.20, 132.10, 134.10, 135.55, 136.16, 149.77, 197.98; LC/MS (ESI): M$^+$, found m/z 381.2, C$_{25}$H$_{19}$NOS requires 381.12.

EXAMPLE 18

Preparation of 3-(1H-indol-3-yl)-3-(3-nitrophenyl)-1-phenylpropan-1-one (3p)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2p (129 mg, 0.425 mmol) in CH$_3$CN (3 mL) were reacted according to GP1. Purification by chromatography on silica gel column (EtOAc/hexanes 1:9) yielded compound 3p as an off-white solid (153 mg, 86%). Enantiomeric excess was determined by chiral HPLC (Chiracel OD-H), hexane:i-PrOH 80:20, 0.4 mL/min, λ=220 nm, t$_r$(minor)=9.137 min, t$_r$(major)=10.186 min to be 97.2%; m.p. 105-107° C., [α]$^{25}_D$=+9.4 (c, 0.45, CHCl$_3$); [Anal. calcd. for C$_{23}$H$_{18}$N$_2$O$_3$: C, 74.58; H, 4.90; N, 7.56; Found C, 74.63; H, 5.11; N, 7.47]. IR (KBr): 3414, 1677, 1536, 1357, 1276, 1133, 724, 519 cm$^{-1}$; $^1$H-NMR (CDCl$_3$, 400 MHz) δ 3.92-4.04 (m, 2H, COCH$_2$), 5.02 (t, 1H, J=6.0 Hz, ArCHCH$_2$), 6.89 (t, 1H, J=6.0 Hz, ArH), 7.02 (t, 1H, J=6.0 Hz, ArH), 7.30 (d, 1H, J=5.6 Hz, ArH), 7.44-7.54 (m, 5H, ArH), 7.61 (t, 1H, J=6.0 Hz, ArH), 7.92-7.95 (m, 2H, ArH), 8.01 (d, 2H, J=5.6 Hz, ArH), 8.22 (s, 1H, ArH), 10.91 (s, 1H, NH of Indole); $^{13}$C-NMR (CDCl$_3$, 100 MHz): δ 37.12, 44.00, 111.87, 117.18, 118.63, 121.08, 121.56, 122.29, 126.16, 128.08, 128.22, 128.63, 128.83, 129.53, 133.71, 134.92, 136.39, 136.70, 139.81, 142.22, 198.10; LC/MS (ESI): M$^+$, found m/z 370.2, C$_{23}$H$_{18}$N$_2$O$_3$ requires 370.13.

EXAMPLE 19

Preparation of 3-(4-bromophenyl)-3-(1H-indol-3-yl)-1-phenylpropan-1-one (3q)

Oxazoline-imidazoline ligand L (17 mg, 0.042 mmol, 10 mol %), Cu(OTf)$_2$ (15 mg, 0.042 mmol, 20 mol %), indole (50 mg, 0.425 mmol) and enone 2q (143 mg, 0.425 mmol) in CH$_3$CN (3 mL) were reacted according to GP1. Purification by chromatography on silica gel column (EtOAc/hexanes 1:9) yielded compound 3q as an off-white solid (158 mg, 82%). Enantiomeric excess was determined by chiral HPLC (Chiracel OD-H), hexane:i-PrOH 80:20, 0.4 mL/min, λ=220 nm, t$_r$(minor)=8.810 min, t$_r$(major)=9.712 min, to be 87.2%; m.p. 95-97° C., [α]$^{25}_D$=+2.8 (c, 0.45, CHCl$_3$); [Anal. calcd. for C$_{23}$H$_{18}$BrNO: C, 68.33; H, 4.49; N, 3.46; Found C, 68.03; H, 4.69; N, 3.34]. IR (KBr): 3366, 1681, 755, 585, 503 cm$^{-1}$; $^1$H-NMR (CDCl$_3$, 400 MHz) δ 4.79 & 3.82 (dd, 1H, J=13.6 Hz, 6.0 Hz, COCH$_{2(a)}$), 3.88 & 3.91 (dd, 1H, J=14.0 Hz, 5.6 Hz, COCH$_{2(b)}$), 4.83 (t, 1H, J=6.0 Hz, ArCHCH$_2$), 6.88 (t, 1H, J=6.4 Hz, ArH), 7.01 (t, 1H, J=6.0 Hz, ArH), 7.28 (d, 1H, J=6.4 Hz, ArH), 7.34-7.39 (m, 6H, ArH), 7.50 (t, 2H, J=6.0 Hz, ArH), 7.61 (t, 1H, J=6.0 Hz, ArH), 7.99 (d, 2H, J=5.6 Hz, ArH), 10.86 (s, 1H, NH of Indole); $^{13}$C-NMR (CDCl$_3$, 100 MHz): δ 36.34, 44.02, 111.91, 117.55, 118.43, 118.64, 119.10, 121.13, 122.15, 126.10, 128.08, 128.73, 130.13, 130.94, 133.22, 136.41, 136.79, 144.78, 198.24; LC/MS (ESI): M+, found m/z 403.1, $C_{23}H_{18}BrNO$ requires 403.06.

EXAMPLE 20

Preparation of 3-(3-bromophenyl)-3-(1H-indol-3-yl)-1-phenylpropan-1-one (3r)

Oxazoline-imidazoline ligand L (17 mg, 0.042 mmol, 10 mol %), $Cu(OTf)_2$ (15 mg, 0.042 mmol, 20 mol %), indole (50 mg, 0.425 mmol) and enone 2r (143 mg, 0.425 mmol) in $CH_3CN$ (3 mL) were reacted according to GP1. Purification by chromatography on silica gel column (EtOAc/hexanes 1:9) yielded compound 3r as an off-white solid (162 mg, 84%). Enantiomeric excess was determined by chiral HPLC (Chiracel OD-H), hexane:i-PrOH 80:20, 0.4 mL/min, λ=220 nm, $t_r$(minor)=9.211 min, $t_r$(major)=10.356 min, to be 89.1%; m.p. 102-104° C., $[\alpha]^{25}_D$=+5.3 (c, 0.45, $CHCl_3$); [Anal. calcd. for $C_{23}H_{18}BrNO$: C, 68.33; H, 4.49; N, 3.46; Found C, 68.17; H, 4.53; N, 3.29]. IR (KBr): 3363, 1683, 744, 587, 501 $cm^{-1}$; $^1$H-NMR ($CDCl_3$, 400 MHz) δ 3.80 & 3.84 (dd, 1H, J=13.6 Hz, 6.4 Hz, $COCH_{2(a)}$), 3.92 & 3.95 (dd, 1H, J=14.0 Hz, 5.6 Hz, $COCH_{2(b)}$), 4.85 (t, 1H, J=6.0 Hz, $ArCHCH_2$), 6.88 (t, 1H, J=6.0 Hz, ArH), 7.01 (t, 1H, J=6.0 Hz, ArH), 7.18 (t, 1H, J=6.4 Hz, ArH), 7.28 (t, 2H, J=5.6 Hz, ArH), 7.37 (d, 1H, J=2.0 Hz, ArH), 7.44 (d, 2H, J=6.4 Hz, ArH), 7.50 (t, 2H, J=6.0 Hz, ArH), 7.57 (s, 1H, ArH), 7.67 (t, 1H, J=6.0 Hz, ArH), 8.00 (d, 2H, J=5.6 Hz, ArH), 10.87 (s, 1H, NH of Indole); $^{13}$C-NMR ($CDCl_3$, 100 MHz): δ 37.01, 44.04, 111.95, 117.48, 118.49, 121.01, 121.54, 122.10, 124.10, 126.26, 127.03, 128.13, 128.75, 129.61, 130.32, 130.56, 133.64, 136.32, 136.79, 148.33, 198.23; LC/MS (ESI): M+, found m/z 403.2, $C_{23}H_{18}BrNO$ requires 403.06.

It is to be understood that the present invention is not limited to the embodiments described above, but encompasses any and all embodiments within the scope of the following claims.

We claim:
1. An enantiomerically pure compound of Formula I:
Formula I

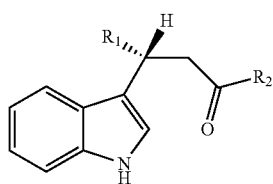

wherein
   $R_1$ is 2,4-dichlorophenyl, or 2,6-dichlorophenyl, and
   $R_2$ is an aryl group or pharmaceutically acceptable salts thereof.

2. The compound according to claim 1, wherein the aryl group of $R_2$ is phenyl or a substituted or unsubstituted naphthyl group.

3. The compound according to claim 1, wherein $R_1$ and $R_2$ are as provided in Table below.

| $R_1$ | $R_2$ |
| --- | --- |
| —$C_6H_3$(2,4-di Cl) | —$C_6H_5$ |
| —$C_6H_3$(2,6-di Cl) | —$C_6H_5$ |

4. A pharmaceutical composition, comprising the compound of claim 1 and a pharmaceutically acceptable carrier.

5. A method for preparing the compound of claim 1, the method comprising:
   (a) mixing a solution of $Cu(OTf)_2$ and a ligand in dry acetonitrile under an inert atmosphere to form a first mixture;
   (b) adding to the first mixture a solution of indole and a conjugated ketone in dry acetonitrile to form a reaction mixture;
   (c) stirring the reaction mixture at ambient temperature for about 24 hours to about 48 hours;
   (d) removing a solvent from the reaction mixture in vacuo; and
   (e) extracting the mixture using an organic solvent.

6. The method of claim 5 further comprising washing the mixture with brine and drying over $MgSO_4$ after extracting the mixture using the organic solvent to isolate the compound of Formula I.

7. The method of claim 6, wherein the organic solvent is ethyl acetate.

8. The method of claim 6, wherein the inert atmosphere is argon atmosphere.

9. The method of claim 6, wherein the ligand is oxazoline-imidazoline.

* * * * *